US006194383B1

(12) United States Patent
Hammann et al.

(10) Patent No.: US 6,194,383 B1
(45) Date of Patent: *Feb. 27, 2001

(54) LIPOPEPTIDES FROM ACTINOPLANES SP. WITH PHARMACOLOGICAL ACTION, PROCESS FOR THEIR PRODUCTION AND THE USE THEREOF

(75) Inventors: Peter Hammann, Babenhausen; Johannes Meiwes, Idstein; Gerhard Seibert, Darmstadt; László Vertesy, Eppstein; Joachim Wink, Rödermark; Astrid Markus, Liederbach, all of (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/811,843

(22) Filed: Mar. 5, 1997

Related U.S. Application Data

(63) Continuation of application No. 08/254,791, filed on Jun. 6, 1994, now abandoned.

(30) Foreign Application Priority Data

Jun. 8, 1993 (DE) .................................................. 43 19 007

(51) Int. Cl.$^7$ ............................. A61K 38/00; C07K 7/64; C12P 21/04
(52) U.S. Cl. .................................. 514/11; 514/9; 514/14; 514/15; 514/2; 530/318; 530/317; 530/359; 435/71.3; 435/71.2; 435/71.1; 435/252.6; 435/252.1; 435/827
(58) Field of Search .................................. 514/11, 9, 14, 514/15, 2; 530/318, 317, 359; 435/71.3, 71.2, 71.1, 252.6, 252.1, 827

(56) References Cited

U.S. PATENT DOCUMENTS

| 4,000,397 | 12/1976 | Herbert et al. . | |
| 4,001,397 | 1/1977 | Celmer et al. | 424/116 |
| 5,629,288 | * 5/1997 | Lattrell et al. | 514/9 |

OTHER PUBLICATIONS

Hausmann et al, The Journal of Antibiotics, vol. XXII,(5), pp. 207–210, (May 1969).*
Kymiakides et al, Biochemistry International, 26, 249–256, (Feb. 1992).*
Geiger et al, The Journal of Biological Chemistry, 262(2) 785–794, (Jan. 15, 1987).*
Inoue, Bulletin of The Chem'l. Soc. of Japan, vol. 35(8), pp. 1249–1254, (Aug. 1962).*
Harold C. Neu, "The Crisis in Antibiotic Resistance," Science, vol. 257, (1992) pp. 1064–1073.
Jun–Ichi Shoji et al., "Isolation and Characterization of an Acidic Acylpeptide Containing a New Fatty Acid," The Journal of Antibiotics, vol. XXI No. 7., (1968) pp. 439–443.
Hiroshi Naganawa et al., "Laspartomycin, A New Anti–Staphylococcal Peptide," The Journal of Antibiotics, vol. XXI No. 1, (1968) pp. 55–62.
A. J. Shay, et al., "Aspartocin. I. Production, Isolation, and Characteristics," Antibiotics Annual (1959–1960) pp. 194–198.
Masahiko Fujino, "On Glumamycin, a New Antibiotic. VI. An Approach to the Amino Acid Sequence," Journal of the American Chemical Society, Japan, vol. 38, No. 4, (1965) pp. 517–522.
Miklos Bodanszky et al., "Structure of the Peptide Antibiotic Amphomycin," Journal of the American Chemical Society vol. 95 No. 7 (1973).
Miklos Bodanszky, "Structure of the Peptide Antibiotic Amphomycin," J. Am. Chem. Soc. vol. 95 No. 7, (1973) pp. 2352–2357.
Hiroshi Naganawa et al., "Novel Fatty Acid from Laspartomycin," Chemical Abstracts vol. 73 No. 21, (1970) Abst. No. 109225k.
Junichi Shoji et al., "Tsushimycin. I. Isolation and Characterization of an Acidic Acylpeptide Containing a New Fatty Acid," Chemical Abstracts vol. 70 No. 11, (1969) Abst. No. 47853r.
W. K. Hausmann et al., "Structure Determination of Fatty Acids from the Antibiotic Aspartocin," Chemical Abstracts vol. 61 No. 6, (1964) Abst. No. 6913b.
Y. Hinuma et al., "Zaomycin, A New Antibiotic From a Streptomyces sp.," Chemical Abstracts vol. 53 No. 2, (1959) Abst. No. 11511b.
G. F. Gauze et al., "Crystallomycin, A New Antibiotic," Chemical Abstracts vol. 53 No. 2, (1959) Abst. No. 8285b.
R.C. Strong et al., "Studies on the Amino Acid Sequence of Amphomycin," Antimicrobial Agents and Chemotherapy—1970, pp. 42–45.

* cited by examiner

Primary Examiner—T. Wessendorf
(74) Attorney, Agent, or Firm—Finnegan, Henderson, Farabow, Garrett and Dunner, L.L.P.

(57) ABSTRACT

The invention relates to lipopeptides with very homologous amino-acid sequences but different fatty acid residues (lipid portion) which are synthesized by Actinoplanes sp. during fermentation and are released into the culture medium, to a process for isolating the lipopeptides from the culture medium and purifying them, to the use of the lipopeptides as pharmacologically active substances, in particular against Gram-positive bacteria, and to Actinoplanes sp. DSM 7358 for producing the abovementioned lipopeptides.

12 Claims, No Drawings

LIPOPEPTIDES FROM ACTINOPLANES SP. WITH PHARMACOLOGICAL ACTION, PROCESS FOR THEIR PRODUCTION AND THE USE THEREOF

This application is a continuation of application Ser. No. 08/254,791, filed on Jun. 6, 1994, now abandoned, which application is entirely incorporated herein by reference.

The invention relates to lipopeptides with very homologous amino-acid sequences but different fatty acid residues (lipid portion) which are synthesized by Actinoplanes sp. during fermentation and are released into the culture medium, to a process for isolating the lipopeptides from the culture medium and purifying them, to the use of the lipopeptides as pharmacologically active substances, in particular against Gram-positive bacteria, and to Actinoplanes sp. DSM 7358 for producing the abovementioned lipopeptides.

Secondary metabolites from microorganisms are successfully employed for the treatment of infectious diseases. Secondary metabolites are low molecular weight compounds whose production takes place in "biosynthetic one-way streets" which branch off from the primary metabolism, and whose function for the particular producer is unclear. To date, about 8000 secondary metabolites isolated from cultures of various microorganisms (especially fungi and bacteria of the genus Streptomyces) are known.

The main area of use of these secondary metabolites is the therapy of infectious diseases. However, owing to the wide use, there is frequently development of resistance so that there is a continuous need for novel antibiotics and active substances with novel mechanisms of action (Neu H. C., Science 257, 1992, pages 1064–1073).

In addition, the area of indications for microbial active substances has also extended to diseases which are not included among infectious diseases (for example tumor therapy, immunomodulation or for the regulation of lipid metabolism) and to crop protection (herbicides and insecticides). However, the active substances which are employed are still frequently associated with deficiencies which are characterized by unsatisfactory effect levels, excessive toxicity and/or unwanted side effects.

There are descriptions in the literature of lipopeptides whose amino-acid content is identical in respect of sequence, or is the same or very similar in respect of amino-acid composition, to the lipopeptides according to the invention. However, these lipopeptides differ fundamentally from the lipopeptides according to the invention in the lipid portion.

Examples of lipopeptides as mentioned above are:
Amphomycin Antibiot. [J. Am. Chem. Soc 95, 2352 (1973)];
Glumamycin [Bull. Chem. Soc. Jap. 38, 517 (1965)];
Zaomycin [J. Antibiot. Ann., page 194 (1960)];
Aspartocin [Antibiot. Ann., 194 (1960)];
Tsuhimycin [J. Antibiotics, 21, page 439 (1968)];
Laspartomycin [J. Antibiotics 21, page 55 (1968)].

These lipopeptides, which are called amphomycin-type lipopeptides, are synthesized by microorganisms of the genus Streptomyces. They display their antibiotic activity against Gram-positive bacterias such as, for example, Strepto-, Staphylo- and Enterococci. Strains of the genera Staphylo- and Enterococcus in particular have proved in recent times to be increasingly problematic organisms. The skilled worker understands problematic organisms to be those microorganisms which it is now impossible to control efficiently because of resistance to conventional antibiotics (for example β-lactam antibiotics or glycopeptide antibiotics such as, for example, vancomycin or teikoplanin).

An example of one group of microorganism strains which have developed resistance comprises the methicillin-resistant Staphylococcus aureus strains, abbreviated to MRSA strains. It is now known that these MRSA strains have often developed resistance not only to methicillin but also to other antibiotics (for example vancomycin).

Apart from the abovementioned compounds from Streptomyces, there is known to be a compound from Actinoplanes nipponensis ATTCC 31145 which, by reason of its spectrum of action and the physicochemical properties described, has structural similarities to the lipopeptides according to the invention and is called compound 41.012 (U.S. Pat. No. 4,001,397). Fermentation of Actinoplanes nipponensis ATCC 31145 under various culture conditions always leads to relatively low yields of compound 41.012.

The object of the invention is to look for microbial natural substances with improved properties.

This object is achieved according to the invention by fermentation of Actinoplanes sp. in a nutrient solution with carbon source and nitrogen source as well as the customary in organic salts, until the lipopeptides, preferably the lipopeptides A 1437, accumulate in the culture medium, subsequent isolation of the lipopeptides from the culture medium and, where appropriate, separation of the mixture into its individual components. The lipopeptides have pharmacological activity and thus therapeutic efficacy and can be employed as antibiotics acting against Gram-positive bacteria, preferably against glycopeptide-resistant strains.

The invention thus relates to:
1. Lipopeptides wherein Actinoplanes sp. is fermented in a culture medium until one or more lipopeptides of the formula I

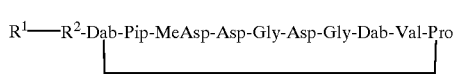

in which
R$^1$ is a singly or multiply unsaturated, saturated or, independently thereof, a branched or unbranched fatty acid or hydroxy fatty acid with a chain length of from 6 to 22, inclusive, carbon atoms
and
R$^2$ is Asp or Asn,
accumulate in the culture medium and, where appropriate, one or more lipopeptides of the formula I are purified from the culture medium, with the exception of the lipopeptide of the formula I in which

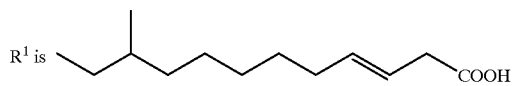

and
R$^2$ is Asp.
2. Lipopeptides wherein Actinoplanes sp. is fermented in a culture medium until one or more lipopeptides from the group:
   a) iC$_{13}$-fatty acid-Asp-Dab-Pip-MeAsp-Asp-Gly-Asp-Gly-Dab-Val-Pro,
   b) iC$_{14}$-fatty acid-Asp-Dab-Pip-MeAsp-Asp-Gly-Asp-Gly-Dab-Val-Pro, c) ic$_{13}$-fatty acid-Asn-Dab-Pip-MeAsp-Asp-Gly-Asp-Gly-Dab-Val-Pro,
d) iC$_{14}$-fatty acid-Asn-Dab-Pip-MeAsp-Asp-Gly-Asp-Gly-Dab-Val-Pro,
e) aiC$_{13}$-fatty acid-Asn-Dab-Pip-MeAsp-Asp-Gly-Asp-Gly-Dab-Val-Pro,
f) aiC$_{15}$-fatty acid-Asp-Dab-Pip-MeAsp-Asp-Gly-Asp-Gly-Dab-Val-Pro,
g) aiC$_{15}$-fatty acid-Asn-Dab-Pip-MeAsp-Asp-Gly-Asp-Gly-Dab-Val-Pro,
h) nC$_{12}$-fatty acid-Asp-Dab-Pip-MeAsp-Asp-Gly-Asp-Gly-Dab-Val-Pro,
i) nC$_{13}$-fatty acid-Asp-Dab-Pi-Me[]sp-Asp-Gly-Asp-Gly-Dab-Val-Pro,
j) nC$_{14}$-fatty acid-Asp-Dab-Pip-MeAsp-Asp-Gly-Asp-Gly-Dab-Val-Pro, accumulate in the culture medium and, where appropriate, one or more of these lipopeptides are purified from the culture medium.

3. Lipopeptides of the formula II,

R$^1$-R$^2$-Dab-Pip-MeAsp-Asp-Gly-Asp-Gly-Dab-Val-Pro     II in which

R$_1$ = 

R$_2$ = Asp or

R$_1$ = 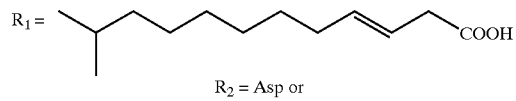

R$_2$ = Asp or

R$_1$ = 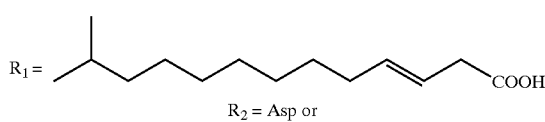

R$_2$ = Asn or

R$_1$ = 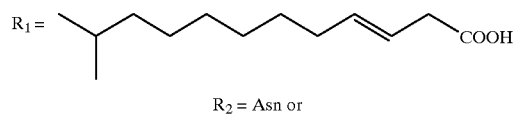

R$_2$ = Asn or

R$_1$ = 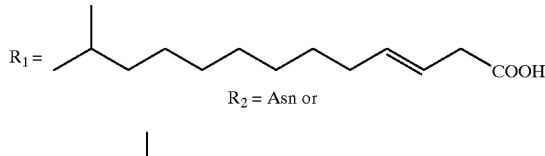

R$_2$ = Asn or

R$_1$ = 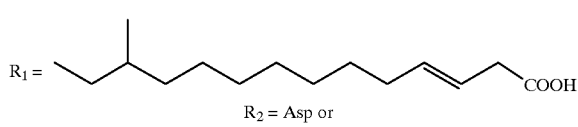

R$_2$ = Asp or

R$_1$ = 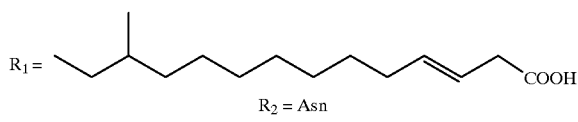

R$_2$ = Asn

R$_1$ =  COOH or

R$_1$ = COOH or

R$_1$ =  COOH and
R$_2$ = Asp in the three last-mentioned cases.

4. A process for the preparation of one or more lipopeptides of the formula I as defined in 1., of one or more lipopeptides as defined in 2., or of one or more lipopeptides of the formula II as defined in 3., which comprises fermenting Actinoplanes sp. in a culture medium until one or more lipopeptides accumulate in the culture medium and, where appropriate, purifying one or more lipopeptides from the culture medium.

5. A use of a lipopeptide of the formula I as pharmacologically active substance, in particular as antibiotic against Gram-positive bacteria, particularly preferably against glycopeptide-resistant bacteria.

6. The use of the lipopeptide of the formula III

R$^1$-R$^2$-Dab-Pip-MeAsp-Asp-Gly-Asp-Gly-Dab-Val-Pro     III in which

R$^1$ is 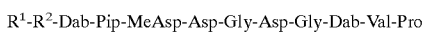

and
R$^2$ is Asp as pharmacologically active substance, in particular as, antibiotic against Gram-positive bacteria, particularly preferably against glycopeptide-resistant bacteria.

7. Actinoplanes sp. DSM 7358.

The invention is described in detail hereinafter, especially in its preferred embodiments. The invention is furthermore defined by the contents of the patent claims.

Definition of terms:
Dab means 2,3-diaminobutyric acid;
Pip means pipecolic acid (synonym=homoproline);
MeAsp means β-methylaspartate;
Gly means glycine;
Asn means asparagine;
Asp means aspartic acid;
Val means valine;
Pro means proline;
n means normal/unbranched and
CID means collisional induced decay.

The abbreviation "i" stands for "iso", while "ai" means "ante-iso". These definitions are known to the skilled worker in the context of fatty acids (Biochemistry, Zubay, published by Addison Wesley in London, Amsterdam, 1983).

Unless otherwise indicated, all percentage data relate to weight. Unless otherwise stated, mixing ratios of liquids relate to volume.

The process according to the invention can be employed for fermentation on the laboratory scale (milliliter to liter range) and for the industrial scale (cubic meter scale).

Actinoplanes sp. is isolated from a soil sample. For purification from the soil the latter is suspended using a physiological NaCl solution (0.9%) with preparation of serial dilutions. The various dilutions ($10^0$–$10^6$) are subsequently plated out on actinomyces nutrient media. Incubation of the cultures at 30° C. for 2 to 14 days results in actinomyces colonies which can be plated out and isolated by a plurality of successive purification steps.

The genera are determined on the basis of morphological and taxonomic criteria using methods known to the skilled worker. Especially characteristic of the genus Actinoplanes are the motile spores.

It is possible on the basis of successive isolation and purification steps to isolate from Actinoplanes sp. a colony which very efficiently releases one or more compounds of the lipopeptides according to the invention, preferably the lipopeptides A 1437 A, B, C, D, E, F, G, H, K, L and/or M, into the culture medium and is called the major producer.

The major producer is the name given to an isolate which produces, or releases into the culture medium, one or more compounds of the lipopeptides according to the invention in an amount which is 10 to 100 times that for isolates of the same Actinoplanes species.

A strongly producing colony of Actinoplanes sp. is propagated. An isolate was deposited at the Deutsche Sammlung von Mikroorganismen und Zellkulturen GmbH, Mascheroder Weg 1B, 3300 Braunschweig, Germany, in accordance with the rules of the Budapest treaty on Jun. 18, 1990, under the following number:
Actinoplanes sp. DSM 7358.

Actinoplanes sp. DSM 7358 has an orange-colored mycelium and is characterized by globose sporangia.

In a nutrient solution (also called culture medium) which contains a carbon source and a nitrogen source as well as the customary inorganic salts, Actinoplanes sp., preferably DSM 7358, produces one or more compounds of the lipopeptides according to the invention.

It is also possible in place of the strain DSM 7358 to employ its mutants and variants which synthesize one or more compounds of the lipopeptides according to the invention. Mutants of this type can be generated in a manner known per se by physical means, for example irradiation, such as with ultraviolet or X-rays, or chemical mutagens such as, for example, ethyl methanesulfonate (EMS), 2-hydroxy-4-methoxybenzophenone (MOB) or N-methyl-N'-nitro-N-nitrosoguanidine (MNNG).

The screening for mutants and variants which synthesize one or more compounds of the lipopeptides according to the invention takes place in accordance with the following scheme:
  removal of the mycelium after the fermentation;
  precipitation of the lipopeptides at pH 1 to 2 (4° C.);
  taking up of the precipitate in $H_2O$/MeOH (1:1);
  analysis by HPLC, TLC or inhibition zone test.

The fermentation conditions described hereinafter apply to Actinoplanes sp., the deposited isolate DSM 7358 and mutants and variants of these.

In a nutrient solution which contains a carbon source and a nitrogen source as well as the customary inorganic salts, Actinoplanes sp., preferably DSM 7358, produces one or more compounds of the lipopeptides according to the invention, but preferably the lipopeptides A 1437 A–H as well as K, L and M.

Suitable and preferred carbon sources for the aerobic fermentation are assimilable carbohydrates and sugar alcohols such as glucose, lactose or D-mannitol, as well as carbohydrate-containing natural products such as, for example, malt extract. Suitable nitrogen-containing nutrients are: amino acids, peptides and proteins as well as their breakdown products such as peptones or tryptones, furthermore meat extracts, milled seeds, for example of corn, wheat, beans, soybean or the cotton plant, distillation residues from the production of alcohol, meat meals or yeast extracts, or else ammonium salts and nitrates. Inorganic salts which the nutrient solution can contain are, for example, chlorides, carbonates, sulfates or phosphates of the alkali metals or alkaline earth metals, iron, zinc, cobalt and manganese.

The production of the lipopeptides according to the invention takes place particularly well in a nutrient solution which contains about 0.1 to 5%, preferably 0.3 to 2%, meat extract and 0.2 to 5%, preferably 0.5 to 2%, sucrose and 0.05 to 5 g/l, preferably 0.1 to 0.5 g/l, yeast extract and 0.05 to 2 g/l, preferably 0.1 to 1 g/l, magnesiumsulfate and 0.05 to 10 g/l, preferably 0.1 to 1 g/l, potassium or sodium dihydrogen phosphate and 0 to 100 $\mu$M, preferably 5 to 20 $\mu$M, iron(III) chloride. The percentage data are in each case based on the weight of the complete nutrient solution.

In this nutrient solution, Actinoplanes sp., preferably Actinoplanes DSM 7358, produces a mixture of the lipopeptides according to the invention. The mixture is preferably composed of 11 different detectable lipopeptides. These lipopeptides have been called A, B, C, D, E, F, G, H, K, L and M. They have the following characteristics:

| Name | $R_1/R_2$ | | Molecular weight |
|---|---|---|---|
| A 1437 A | $R_1$ = (structure shown) $R_2$ = Asp | | 1290 |
| A 1437 B | $R_1$ = (structure shown) $R_2$ = Asp | | 1304 |
| A 1437 C | $R_1$ = (structure shown) $R_2$ = Asn | | 1289 |

-continued

| Name | $R_1/R_2$ | | Molecular weight |
|---|---|---|---|
| A 1437 D | $R_1 =$ (structure) $R_2 =$ Asn | | 1303 |
| A 1437 E | $R_1 =$ (structure) $R_2 =$ Asp | | 1290 |
| A 1437 F | $R_1 =$ (structure) $R_2 =$ Asn | | 1289 |
| A 1437 G | $R_1 =$ (structure) $R_2 =$ Asp | | 1318 |
| A 1437 H | $R_1 =$ (structure) $R_2 =$ Asn | | 1317 |
| A 1437 K | $R_1 =$ (structure) $R_2 =$ Asp | | 1318 |
| A 1437 L | $R_1 =$ (structure) $R_2 =$ Asp | | 1318 |
| A 1437 M | $R_1 =$ (structure) $R_2 =$ Asp | | 1318 |

Lipopeptide A 1437 A contains, as does A 1437 C, an iso-$C_{13}$-fatty acid which has not hitherto been known in lipopeptides of the amphomycin type. The amino-acid sequence of A 1437 A corresponds to that of amphomycin which, however, contains an ante-iso-$C_{13}$-fatty acid. The amino-acid composition and sequence of A 1437 C are not known from other lipopeptides.

A 1437 B contains, as does A 1437 D, a fatty acid of the iso-$C_{14}$ type and thus the fatty acid known from tsushimycin. However, A 1437 D differs in its amino-acid composition and sequence from the lipopeptides hitherto known from the prior art, whereas A 1437 B contains the amino-acid sequence of amphomycin. According to the literature, amphomycin, zaomycin and tsushimycin are identical in amino-acid composition.

A 1437 E from Actinoplanes sp., in particular from Actinoplanes DSM 7358, is identical to the amphomycin known from streptomyces.

A 1437 F comprises an ante-iso-$C_{13}$-fatty acid and thus therefore contains the same fatty acid type as known from amphomycin. Its amino-acid sequence and composition are unknown from the prior art.

The lipopeptides A 1437 G and A 1437 H each have, as does aspartocin, an ante-iso-$C_{15}$-fatty acid. The amino-acid sequence of A 1437 G corresponds to that of amphomycin, whereas the sequence and composition of A 1437 H are unknown from the prior art.

A 1437 K, L and M have unbranched fatty acids with a chain length of $C_{12}$–$C_{14}$. The amino-acid sequence of the three lipopeptides mentioned corresponds to that of amphomycin.

The lipopeptides A 1437 A to H all have a linkage of the carboxyl functionality of the C-terminal proline to the β-amino functionality of the Dab located at the amino terminus. This linkage is represented by "⌊⌋".

The content in terms of quantity of one or more of the lipopeptides according to the invention may vary depending on the composition of the nutrient solution. In addition, it is possible to control the synthesis of individual lipopeptides by the composition of the medium so that the microorganism does not produce a lipopeptide at all or produces it in an amount below the detection limit.

The culture medium from Actinoplanes sp., preferably DSM 7358, contains lipopeptides with a singly or multiply unsaturated, saturated or, independently thereof, a branched or unbranched fatty acid or hydroxy fatty acid with a chain length of from 6 to 22, inclusive, carbon atoms, preferably from 10 to 20, inclusive, carbon atoms, particularly preferably of 13, 14 or 15 carbon atoms.

Fatty acids of these types are known to the skilled worker, for example from Römpp Chemie Lexikon, Prof. Falbe and Prof. Regitz, 9th edition, Georg Thieme Verlag Stuttgart, New York or from, The Encyclopedia of Chemistry, C. A. Hempel and G. G. Hawley, 3rd edition, Van Nostrand Reinhold Company, New York.

The following list of fatty acids is by way of example, makes no claim to completeness and represents no restriction.

Examples of saturated unbranched fatty acids on the lipopeptides according to the invention are caproic, enanthic, caprylic, pelargonic, capric, undecanoic, lauric, tridecanoic, myristic, pentadecanoic, palmitic, margaric, stearic, nonadecanoic, arachic and behenic acid.

Examples of saturated branched fatty acids on the lipopeptides according to the invention are isobutyric or isovaleric acid or the corresponding acids in the "ante-iso" configuration.

Examples of singly unsaturated unbranched fatty acids on the lipopeptides according to the invention are acrylic or crotonic acid.

An example of a doubly unsaturated unbranched fatty acid on the lipopeptides according to the invention is sorbic acid.

Examples of triply unsaturated unbranched fatty acids on the lipopeptides according to the invention are linolenic or eleostearic acid.

An example of a four-fold unsaturated unbranched fatty acid on the lipopeptides according to the invention is arachidonic acid.

An example of a five-fold unsaturated unbranched fatty acid on the lipopeptides according to the invention is clupanodenic acid.

An example of a six-fold unsaturated unbranched fatty acid on the lipopeptides according to the invention is docosahexaenoic acid.

It is furthermore possible for the lipopeptides with multiply branched fatty acids such as, for example, 2, 4, 6, 8-tetramethyldecanoic acid to occur in the culture medium.

Examples of hydroxy fatty acids on the lipopeptides according to the invention are fatty acids which are hydroxylated at position 2 and 3 and/or at the end of the carbon chain and have the "iso" or "ante-iso" configuration.

On addition of 0.01 to 5%, preferably 0.02 to 0.1%, L-valine to the nutrient solution described above, the strain Actinoplanes sp. preferentially produces the lipopeptides A 1437 B and D. On addition of 0.01 to 5%, preferably 0.1 to 0.5%, L-leucine to the nutrient solution described above, the strain Actinoplanes sp. preferentially produces the lipopeptides A 1437 A and C. On addition of 0.01 to 5%, preferably 0.05 to 0.5%, L-isoleucine to the nutrient solution described above, the strain Actinoplanes sp. produces in particular the lipopeptides A 1437 E, F, G and R. On addition of 0.01 to 5%, preferably 0.05 to 0.5%, L-α-aminobutyric acid to the nutrient solution described above, the strain Actinoplanes sp. preferentially produces lipopeptide K. On addition of 0.01 to 5%, preferably 0.05 to 0.5%, L-norvaline to the nutrient solution described above, the strain Actinoplanes sp. preferentially produces the lipopeptides L and/or M. The same applies to the preferred strain DSM 7358.

Besides these amino acids it is also possible to employ the α-keto acids corresponding to the said amino acids (α-ketoisovalerate, α-ketoisocaproate, α-keto-β-methylvalerate, α-ketovalerate) or their corresponding acids (isobutyrate, isovalerate, α-methylbutyrate, n-butyrate, propionate, valerate) in the appropriate concentrations or other substances which can intervene in fatty acid biosynthesis.

The microorganism cultivation takes place aerobically, that is to say, for example, submerged with shaking or stirring in shaken flasks or fermenters, where appropriate with introduction of air or oxygen. It can be carried out in a temperature range from about 18 to 35° C., preferably at about 25 to 35° C., in particular at 28 to 32° C. The pH range ought to be between 6 and 8, preferably between 6.5 and 7.5. The microorganism is cultivated under these conditions in general for a period of from 24 to 300 hours, preferably 36 to 140 hours.

The cultivation is advantageously carried out in several stages, i.e. one or more precultures are initially prepared in a liquid nutrient medium and are then transferred into the actual production medium, the main culture, for example in the ratio 1:10 by volume. The preculture is obtained, for example, by transferring a mycelium into a nutrient solution and allowing it to grow for about 36 to 120 hours, preferably 48 to 72 hours. The mycelium can be obtained, for example, by allowing the strain to grow for about 3 to 40 days, preferably 4 to 10 days, on a solid or liquid nutrient medium, for example yeast-malt agar or nutrient broth agar (standard medium for microorganisms with the main constituents peptone, sodium chloride and agar, for example supplied by Difco).

The progress of the fermentation can be monitored on the basis of the pH of the cultures or of the volume of the mycelium, as well as by chromatographic methods such as, for example, thin-layer chromatography or high pressure liquid chromatography or testing the biological activity. Both the mycelium and the culture filtrate contain a compound according to the invention, but most ($\geq 90\%$) is located in the culture filtrate.

The isolation process described hereinafter is used to purify the lipopeptides according to the invention, but preferably for the lipopeptides A 1437 A–H as well as K, L and M.

The isolation or purification of a lipopeptide according to the invention from the culture medium takes place by known methods taking account of the chemical, physical and biological properties of the natural substances. The antibiotic concentration in the culture medium or in the individual isolation stages can be tested by thin-layer chromatography, for example on silica gel with isopropanol/25% strength $NH_3$ as mobile phase or HPLC. In the fractionation by thin-layer chromatography, the detection can take place, for example, by color reagents such as anisaldehyde, in which case the amount of the produced substance is expediently compared with a calibration solution.

To isolate a lipopeptide according to the invention, the mycelium is initially separated from the culture broth by the customary processes, and subsequently the culture filtrate is adjusted, preferably at 4° C., to a pH from pH 0.5 to pH 4, inclusive, preferably from pH 1.5 to pH 2.5, inclusive. The adjustment of the pH, and thus the precipitation of the lipopeptides A 1437, can take place with all commercially available acids. The solution is incubated for up to 16 h, preferably up to 4 h, and subsequently the resulting precipitate is removed by centrifugation.

The precipitate, which contains all the lipopeptides, is resuspended in 1/20 of the original volume of double-distilled water and adjusted to pH 6 to 7 with NaOH. This results in the precipitate completely dissolving; the solution is cooled to −20° C. and lyophilized. The lyophilizate, which is called the crude product hereinafter, contains 5 to 30% lipopeptides and is employed for the subsequent isolation.

Further purification of one or more lipopeptides according to the invention takes place by chromatography on suitable materials, preferably, for example, on silica gel, aluminum oxide, ion exchangers or adsorber resins and very particularly preferably on strongly or weakly basic anion exchangers. The lipopeptides which contain Asp or Asn as amino acid located at the amino terminus are separated by means of this chromatography. The chromatography of the lipopeptides is carried out with buffered aqueous solutions or mixtures of aqueous and alcoholic solutions.

Buffered aqueous solutions mean, for example, water, phosphate buffer, ammonium acetate, citrate buffer, borate buffer in a concentration of from 0 to 1 M, preferably 1 to 100 mM, and phosphate-buffered solutions with a concentration of 1 to 100 mM are particularly preferably employed.

Mixtures of aqueous or alcoholic solutions mean all organic solvents which are miscible with water, preferably methanol, acetonitrile, in a concentration of from 10 to 80% solvent, preferably 40 to 60% solvent, or else all buffered aqueous solutions which are miscible with organic solvents. The buffers to be used are the same as indicated above.

The separation of the lipopeptides on the basis of their different fatty acids takes place with the aid of reversed phase chromatography, for example on MCI® (adsorber resin from Mitsubishi, Japan). Reversed phase chromatography on hydrophobic materials, preferably RP-8 or RP-18 phase chromatography, is particularly preferred. In addition, the separation can take place with the aid of silica gel chromatography.

The chromatography of the lipopeptides takes place with buffered or acidified aqueous solutions or mixtures of aqueous solutions with alcohols or other organic solvents which are miscible with water. Acetonitrile is preferably used as organic solvent.

Buffered or acidified aqueous solutions mean, for example, water, phosphate buffer, ammonium acetate, citrate buffer, borate buffer in a concentration of 0 to 0.5 M as well as formic acid, acetic acid, trifluoroacetic acid or all commercially available acids known to the skilled worker, preferably in a concentration of from 0 to 1%. 0.1% is particularly preferred.

Chromatography is carried out with a gradient which starts with 100% water and finishes with 100% solvent, and a linear gradient from 40 to 60% acetonitrile is preferably applied.

The sequence of the two abovementioned chromatographies (chromatography to separate the lipopeptides according to the amino acids Asp or Asn and according to the fatty acid type) can be reversed. It is preferable to separate the lipopeptides according to different amino acids in the first step and only subsequently to separate them according to the fatty acid type.

If the abovementioned crude product contains lipopeptides with uniform fatty acid, the previously described chromatography (separation of the lipopeptides on the basis of different fatty acids) is employed for the desalting and further purification of the lipopeptides.

An alternative possibility is also gel chromatography or chromatography on hydrophobic phases.

Gel chromatography is carried out on polyacrylamide or mixed polymer gels such as, for example, BIOGEL-P 2® (supplied by Biorad) or FRACTOGEL TSK HW 40® (supplied by Merck, Germany or Toso Haas, USA).

The lipopeptides according to the invention are stable in the solid state and in solutions in the pH range between 4 and 8, in particular 5 and 7, and can therefore be incorporated into customary pharmaceutical formulations.

One or more compounds of the lipopeptides according to the invention are suitable by reason of their valuable pharmacological properties for use as pharmaceuticals.

The substances according to the invention have pharmacological activity in particular as antibiotic against Gram-positive bacteria, particularly preferably against glycopeptide-resistant strains.

A therapeutically adequate effect on penicillin- or methicillin-resistant strains (MRSA strains) which have developed further resistance to antibiotics is frequently possessed only by glycopeptides such as vancomycin or teicoplanin. However, strains resistant even to these antibiotics are increasingly appearing (FEMS Microbiol. Lett. 98 (1992) 109 to 116). One or more compounds of the lipopeptides according to the invention have an excellent effect against these problematic organisms too.

The invention also relates to pharmaceutical formulations of one or more compounds of the lipopeptides according to the invention.

It is possible in principle to administer one or more compounds of the lipopeptides according to the invention, preferably one or more compounds of the lipopeptides A 1437 A–H, undiluted as such. Use in a mixture with suitable ancillary substances or carrier material is preferred. Carrier material which can be used in the case of veterinary pharmaceuticals comprises customary feed mixtures, and in the case of humans comprises all pharmacologically compatible carrier materials and/or ancillary substances.

The pharmaceuticals according to the invention are generally administered orally or parenterally, but rectal use is also possible in principle. Examples of suitable solid or liquid pharmaceutical presentations are granules, powders, tablets, coated tablets, (micro) capsules, suppositories, syrups, emulsions, suspensions, aerosols, drops or injectable solutions in ampoule form as well as products with protracted release of active substance, in whose production it is normal to use vehicles and additives and/or auxiliaries such as disintegrants, binders, coating agents, swelling agents, glidants or lubricants, flavorings, sweeteners or solubilizers. Examples of vehicles or ancillary substances which are frequently used and which may be mentioned are magnesium carbonate, titanium dioxide, lactose, mannitol and other sugars, talc, lactalbumin, gelatin, starch, vitamins, cellulose and its derivatives, animal or vegetable oils, polyethylene glycols and solvents such as, for example, sterile water, alcohols, glycerol and polyhydric alcohols.

It is possible where appropriate for the dosage units for oral administration to be microencapsulated in order to delay release or extend it over a longer period, such as, for example, by coating or embedding the active substance in particulate form in suitable polymers, waxes or the like.

The pharmaceutical products are preferably produced and administered in dosage units, with each unit containing as active ingredient a particular dose of one or more compounds of the lipopeptides according to the invention.

In the case of solid dosage units such as tablets, capsules and suppositories, this dose can be up to about 200 mg, but preferably about 0.1 to 100 mg, and in the case of injection solutions in ampoule form up to about 200 mg, but preferably about 0.5 to 100 mg, per day.

The daily dose to be administered depends on the body weight, age, sex and condition of the mammal. However, in some circumstances, higher or lower daily doses may also be appropriate. Administration of the daily dose can take place either by a single administration in the form of a single dosage unit or else in a plurality of smaller dosage units as well as by multiple administration of divided doses at particular intervals.

The pharmaceuticals according to the invention are produced by converting one or more compounds of the lipopeptides according to the invention into the or a suitable dosage form using customary vehicles as well as, where appropriate, additives and/or ancillary substances.

The invention is explained further in the examples which follow. Percentage data relate to weight. Unless stated otherwise, mixing ratios of liquids relate to volume.

EXAMPLES

1a) Preparation of a glycerol culture of Actinoplanes sp. DSM 7358

100 ml of nutrient solution (4 g/l yeast extract, 15 g/l soluble starch, 1 g/l $K_2HPO_4$, 0.5 g/l $MgSO_4 \times 7\ H_2O$ made up to 1000 ml with water, pH before sterilization 7.0) in a sterile 300 ml Erlenmeyer flask are inoculated with the strain Actinoplanes sp. DSM 7358 and incubated on a rotating shaker at 30° C. and 150 rpm for 7 days. 1.5 ml of this culture are subsequently diluted with 2.5 ml of 80% strength glycerol and stored at −20° C.

1b) Preparation of a culture or of a preculture of Actinoplanes sp. DSM 7358 in an Erlenmeyer flask:

A sterile 300 ml Erlenmeyer flask containing 100 ml of the following nutrient solution: 30 g/l sucrose, 2 g/l $KNO_3$, 1 g/l $K_2HPO_4$, 0.5 g/l $MgSO_4 \times 7\ H_2O$, 0.5 g/l KCl, 0.01 g/l $FeSO_4 \times 7\ H_2O$, 2 g/l yeast extract, 5 g/l peptone is inoculated with a culture grown in a slant tube (same nutrient solution but with 2% agar) or with 1 ml of a glycerol culture (see Example 1a) and incubated in a shaker at 180 rpm and 30° C. The maximum production of one or more compounds of the lipopeptides according to the invention is reached after about 120 hours. A submerged culture which is 48 to 96 h old (inoculum about 10%) from the same nutrient solution suffices to inoculate 10 and 200 l fermenters.

2) Comparative characterization of Actinoplanes sp. DSM 7358

The strain Actinoplanes sp. DSM 7358 is characterized by comparison with closely related strains by the Shirling and Gottlieb ISP method (Int. J. of Sys. Bacteriol. 16, 3 (1966) 313 to 340). The results (see Tab. 1) show that the strain Actinoplanes sp. DSM 7358 differs morphologically and in its physiology from the other strains.

TABLE 1

|  | Actinoplanes sp. DSM 7358 | Actinoplanes sp. NRRL 12052 | Actinoplanes sp. ATCC 25844 | Actinoplanes sp. ATCC 311455 |
| --- | --- | --- | --- | --- |
| *Aerial mycelium* | − | − | + (ISP 3) | − |
| Sporangia | + | + | + | + |
| Medium |  |  |  |  |
| ISP 2 | orange | orange | yellowish orange | orange |
| ISP 3 | orange | orange | yellowish orange | orange |
| ISP 4 | orange | orange | yellowish orange | orange |
| ISP 5 | orange | orange | yellowish orange | orange |
| ISP 6 | orange red exopigment | orange brownish red exopigment | yellowish orange red exopigment | orange red exopigment |
| Melanin | − | − | (+) | (+) |
| Glucose | + | + | + | + |
| Arabinose | + | + | + | + |
| Sucrose | + | + | + | + |
| Xylose | + | + | (+) | − |
| Inositol | + | + | (+) | (+) |
| Mannitol | + | + | + | − |
| Fructose | + | + | + | − |
| Rhamnose | + | + | + | + |
| Raffinose | + | + | (+) | − |
| Cellulose | + | + | (+) | − |
| Melibiose | − | − | − | − |
| Amygdalin | − | + | + | + |
| Gelatin (hydrolysis) | + | + | + | + |
| Citrate (hydrolysis) | − | − | + | − |
| Urea (hydrolysis) | + | − | − | − |
| Arginine hydrolase | + | − | − | − |
| β-Galactosidase | − | − | − | − |
| Tryptophanase | − | − | − | − |
| Lysine decarboxylase | + | − | − | − |
| Acetoin (formation) | + | + | + | + |
| Indole (formation) | − | − | − | − |
| $H_2S$ (formation) | − | − | − | − |
| NaCl tolerance | 0–2.5% | 0–2.5% | 0–2.5% | 0–2.5% |

3a) Preparation of the lipopeptides A 1437 B and D

A 500 l fermenter is operated under the following conditions:

| | |
|---|---|
| Nutrient medium: | 11 g/l sucrose |
| | 6 g/l meat extract |
| | 0.3 g/l yeast extract |
| | 0.6 g/l MgSO$_4$ |
| | 0.1 g/l KH$_2$PO$_4$ |
| | 10 μM FeCl$_3$ × 6H$_2$O |
| | 0.6 g/l L-valine |
| | pH 7.3 (before sterilization) |
| Incubation time: | 120 hours |
| Incubation temperature: | 30° C. |
| Stirrer speed: | 50 rpm |
| Aeration: | 150 l min$^{-1}$ |

Foaming can be suppressed by repeated addition of ethanolic polyol solution. The maximum production is reached after about 96 to 120 hours.

After completion of the fermentation of Actinoplanes sp. DSM 7358, the culture broth is filtered with the addition of about 2% of filtration aid (for example CELITE®) and the culture filtrate is cooled to 4° C. and adjusted to a pH of 1.5. After 4 h, the mixture is centrifuged at 10,000 g and the precipitate is resuspended in distilled water. Neutralization of the suspension results in the said substance going into solution. The latter is frozen and lyophilized. The yield is about 1.5 g/l crude product (=750 g).

3b) Fractionation of the crude product (contains B+D) by ion chromatography

A 3.2 l chromatography column (10 cm ID×40 cm H) is packed with DEAE-®SEPHAROSE Fast Flow and equilibrated with 10 mM potassium phosphate buffer, pH 7.0, in 40% methanol (buffer A). Then 25 g of A 1437 B crude product (obtained as in Example 3a), dissolved in 3.5 l of water, are loaded onto the column and washed with 1 l of water and subsequently with 6 l of buffer A. Impurities in the crude product are present in the flow-through and in the aqueous washings. Subsequently, a gradient from 10 to 100 mM potassium phosphate, pH 7.0, in 40% methanol is applied. The A 1437 D peptide is eluted with 25 to 35 mM potassium phosphate, and the antibiotic A 1437 B is obtained with 40 to 55 mM potassium phosphate. Methanol is removed from the appropriate fractions in vacuo. A ®DIANION HP-20 column (Mitsubishi, Japan) with a capacity of 1 l is used for desalting. 9 l of the fractions containing pure B peptide are now loaded onto the column and subsequently washed with 3 l of deionized water. Water/isopropanol is used for elution by the gradient method (0 to 50% alcohol contents). Pure A 1437 B is washed off the support with 15 to 25% isopropanol. This eluate from the column is collected separately, concentrated in vacuo and freeze-dried. The result is 4.8 g of A 1437 B with a purity of 97%. Corresponding desalting of the fractions containing A 1437 D yielded 3.1 g of the antibiotic. Purity 98%.

4a) Preparation of the lipopeptides A 1437 A and C

Preparation takes place as described under 3a, merely replacing L-valine in the production medium by 4 g/l L-leucine and carrying out the fermentation in a 50 l bioreactor. The yield is 1.3 g/l crude peptide (=65 g).

4b) Isolation of the lipopeptides A 1437 A and C 10 g of the crude product were dissolved in 100 ml of distilled water and worked up in accordance with the scheme shown below.

Work-up scheme:

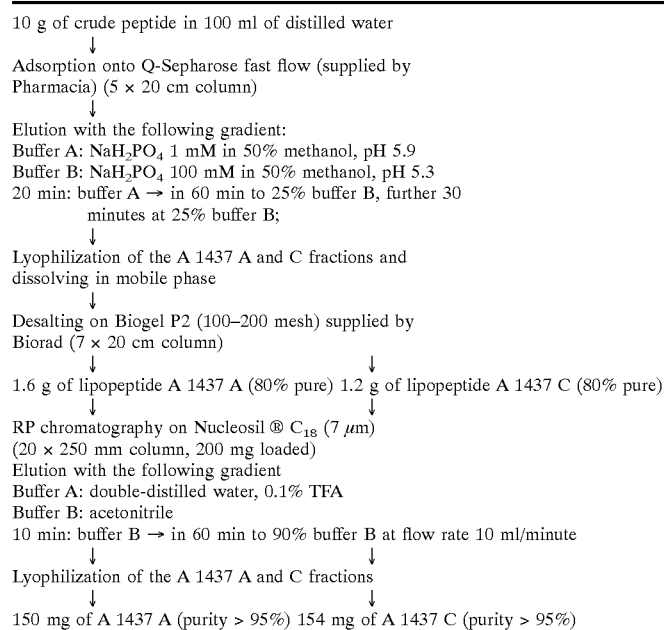

10 g of crude peptide in 100 ml of distilled water
↓
Adsorption onto Q-Sepharose fast flow (supplied by Pharmacia) (5 × 20 cm column)
↓
Elution with the following gradient:
Buffer A: NaH$_2$PO$_4$ 1 mM in 50% methanol, pH 5.9
Buffer B: NaH$_2$PO$_4$ 100 mM in 50% methanol, pH 5.3
20 min: buffer A → in 60 min to 25% buffer B, further 30 minutes at 25% buffer B;
↓
Lyophilization of the A 1437 A and C fractions and dissolving in mobile phase
↓
Desalting on Biogel P2 (100–200 mesh) supplied by Biorad (7 × 20 cm column)
↓                                                      ↓
1.6 g of lipopeptide A 1437 A (80% pure)   1.2 g of lipopeptide A 1437 C (80% pure)
↓
RP chromatography on Nucleosil ® C$_{18}$ (7 μm)
(20 × 250 mm column, 200 mg loaded)
Elution with the following gradient
Buffer A: double-distilled water, 0.1% TFA
Buffer B: acetonitrile
10 min: buffer B → in 60 min to 90% buffer B at flow rate 10 ml/minute
↓                                                      ↓
Lyophilization of the A 1437 A and C fractions
↓                                                      ↓
150 mg of A 1437 A (purity > 95%)   154 mg of A 1437 C (purity > 95%)

5a) Preparation of the lipopeptides A 1437 E, F, G and H

Preparation takes place as described in Example 3a, merely replacing the L-valine in the production medium by 1.5 g/l L-isoleucine and carrying out the fermentation in a 50 l bioreactor. The yield is 1.4 g/l crude peptide (70 g).

5b) Fractionation of the crude peptide by ion chromatography 25 g of lipopeptide crude product obtained as in Example 5a are fractionated in accordance with Example 3a on the column described in Example 3a.

Lipopeptide A 1437 F (yield: 1.8 g) is eluted with 14 to 19 mM buffer,
A 1437 E (yield: 1.3 g) is eluted with 18 to 25 mM buffer,
A 1437 H (yield: 2.7 g) is eluted with 35 to 50 mM buffer and
A 1437 G (yield: 1.9 g) is eluted with 64 to 82 mM buffer.

The corresponding fractions are combined and methanol is removed in vacuo.

5c) Purification of the components from Example 5b on reverse phase RP-18

A preparative HPLC column (5.1 cm (ID)×25 cm H) with a capacity of 500 ml is packed with ®LiChrosorbG RP-18, 10 μm, and the salt-containing solution containing 1.9 g of the antibiotic A 1437 G is loaded on. Elution is by the gradient method with 5% acetonitrile in 10 mM potassium phosphate buffer, pH 7.0 to 36% acetonitrile in 10 mM potassium phosphate buffer, pH 7.0. Lipopeptide A 1437 G is obtained with 24 to 26% acetonitrile. Concentration in vacuo, desalting on 100 ml of ®Dianion HP-20 adsorption resin in the water/50% isopropanol system and freeze-drying result in 1.1 g of lipopeptide A 1437 G in a purity of 99%.

Corresponding subsequent purification of the A 1437 H solution obtained as in Example 5b takes place with the solvent gradient from 10 to 50% acetonitrile in 10 mM potassium phosphate buffer, pH 7.0. The antibiotic is eluted with solvent contents from 37 to 39%.

Concentration of the appropriate fractions and desalting on ®Dianion HP-20, as well as freeze-drying, yield 2.2 g of lipopeptide A 1437 H in a purity which is above 98%.

5d) Purification of the lipopeptide antibiotics A 1437 E and F from Example 5b on MCI gel The salt-containing solution containing 1.8 g of the antibiotic A 1437 F obtained as in Example 5b is loaded onto 1 l of MCI gel CEP 20P (Mitsubishi Kasci Corp.). The column dimensions are 6 cm ID×35 cm H. After the support has been loaded with the material to be separated it is washed with buffer A (5 mM potassium phosphate buffer pH 7.0 with 20% acetonitrile) and eluted by a method with a gradient to buffer B (5 mM potassium phosphate buffer, pH 7.0, with 70% acetonitrile). Solvent contents of 34 to 35% lead to elution of the pure antibiotic. Concentration in vacuo and desalting on ®Dianion HP-20 yield 1.4 g of lipopeptide A 1437 F in a purity which is above 98%. The analogous procedure with the A 1437 E crude product from Example 5a yields 1 g of lipopeptide A 1437 E in a purity which is above 98%.

6a) Preparation of the lipopeptide A 1437 K

Preparation takes place as described under 4a, merely replacing the L-valine in the production medium by 500 mg/l L-α-aminobutyric acid (or 1 g/l of the racemate) and carrying out the fermentation in a 10 l bioreactor. The yield is 1.1 g/l crude peptide (=10 g).

6b) Isolation of the lipopeptide A 1437 K 10 g of the crude product were dissolved in 100 ml of distilled water and worked up in accordance with the scheme below.

Work-up scheme (A 1437 K)
  10 g of crude peptide in 100 ml of distilled water
  adsorption onto Q-Sepharose fast flow (3.5×17 cm column)
  Elution with the following gradient
  Buffer A: $NaH_2PO_4$ 1 mM in 50% methanol, pH 5.9
  Buffer B: $NaH_2PO_4$ 100 mM in 50% methanol, pH 5.93
  20 min: buffer A→in 45 min to 25% buffer B, further 45 min at 25% buffer B
  Lyophilization of the A 1437 K fractions
  Desalting on Biogel P2 (100–200 mesh) (7×20 cm column) 700 mg of A 1437 K (60% pure)
  RP chromatography on Nucleosil $C_{18}$ 7 μm (20×250 mm column)
  Loading: 50 mg of the prepurified product
  Elution with the following gradient
  Buffer A: double-distilled water, 0.1% TFA
  Buffer B: acetonitrile
  10 min: buffer A/5% buffer B→in 60 min to 70% buffer B at flow rate 10 ml/min
  Lyophilization of the A 1437 K fractions 5.6 mg of A 1437 K (>95% pure)

7a) Preparation of the lipopeptides A 1437 L and M

Preparation takes place as described under 4a, merely replacing the L-valine in the production mixture by 500 mg/l L-norvaline (or 1 g/l of the racemate) and carrying out the fermentation in a 10 l bioreactor. The yield is 1.2 g/l crude peptide (=12 g).

7b) Isolation of the lipopeptides A 1437 L and M 10 g of the crude product are dissolved in 100 ml of distilled water and worked up in accordance with the scheme below.

Work-up scheme:
  10 g of crude peptide in 100 ml of distilled water
  Adsorption onto the Q-Sepharose fast flow (3.5×17 cm column)
  Elution with the following gradient
  Buffer A: $NaH_2PO_4$ 1 mM in 50% methanol, pH 5.9
  Buffer B: $NaH_2PO_4$ 100 mM in 50% methanol, pH 5.3
  20 min: buffer A→in 45 min to 25% buffer B, further 45 min at 25% buffer B
  Lyophilization of the A 1437 L and M fractions
  Desalting on Biogel P2 (100–200 mesh) (7×20 cm column) 900 mg of A 1437 L and M (about 60% pure)
  RP chromatography on Nucleosil $C_{18}$ 7 μm (20×250 mm column)
  Loading: 50 mg of the prepurified product
  Elution with the following gradient
  Buffer A: double-distilled water, 0.1% TFA
  Buffer B: acetonitrile
  10 min: buffer A/5% buffer B→in 60 min to 70% buffer B at flow rate 10 ml/minute
  Lyophilization of the A 1437 L and M fractions
  5.8 mg of A 1437 L (>95% pure) 6.7 mg of A 1437 M (>95% pure)

8) HPLC system for detecting the A 1437 lipopeptides

The system described below allows the lipopeptides in the crude mixture and in the culture filtrate to be separated and quantified; the retention times are between 11.5 minutes (A 1437 E) and about 15.9 minutes (A 1437 H).

| Mobile phases: | A | potassium phosphate buffer pH 7.0, 10 mM | | |
| --- | --- | --- | --- | --- |
| | B | acetonitrile | | |
| Gradient: | t[min] | Flow rate [ml/min] | A[%] | B[%] |
| | 0 | 1.5 | 80 | 20 |
| | 15 | 1.5 | 50 | 50 |
| | 15.5 | 2 | 00 | 100 |
| | 16.5 | 2 | 00 | 100 |
| | 17 | 1.5 | 80 | 20 |
| | 22 | 1.5 | 80 | 20 |

-continued

| Column: | Shandon ODS Hypersil RP 18 (120 × 4.6 mm with 20 × 4.6 mm precolumn) or Nucleosil 120 RP 18 (120 × 4.6 mm with 20 × 4.6 mm precolumn) |
|---|---|
| Flow rate: | 1.5 ml/min |
| Detection: | 210 nm |
| Injection: | 10 μl |

9) Comparison between Actinoplanes nipponensis ATCC 31145 and Actinoplanes spec. DSM 7358

Initially a preculture is grown of the two strains as described in Example 1b and used to inoculate the following production media.

Medium 1: as described in Example 3a
Medium 2: as medium 1 but without L-valine
Medium 3: glucose 30 g/l; soybean meal 20 g/l; $Fe_2(SO_4)_3$ 0.3 g/l; $MnCl_2 \times 4H_2O$ 0.3 g/l and $CoCl_2 \times 6H_2O$, pH 7.3 in each case 100 ml of medium in a 300 ml Erlenmeyer flask.

Incubation takes place at 30° C. in a rotating shaker. The concentration of the A 1437 lipopeptides in the culture filtrate in determined by HPLC (see Example 8) after 48, 96 and 144 hours. No lipopeptide whatsoever is detectable in medium 2 and medium 3 with the strain Actinoplanes nipponensis ATCC 31145. In medium 1 it is possible after 144 hours to detect a few peptides in very small amounts. Assuming that the specific extinction of these compounds is identical to that of the A 1437 peptides, the amount produced is a factor of at least 100 (<1 mg/l) below the concentration of A 1437 B synthesized by the strain Actinoplanes spec. DSM 7358 in medium 1 after the same time.

10) Effect of the A 1437 lipopeptides

The sensitivity of relevant organisms to the A 1437 lipopeptides is determined by an agar dilution test. The agar used is Müller-Hinton agar to which, in the case of S. pyogenes and the Enterococci, 10% horse blood is added. The antibiotic-containing plates are inoculated using a multichannel inoculator ($5 \times 10^4$ cfu/inoculation site of a stationary culture of the particular strain). The MIC values (minimum inhibitory concentration) are read off at 37° C. The MIC is defined as the concentration of the antibiotic at which no visible growth of the organisms is detectable after incubation for 24 hours. The results are compiled in Table 2. The amphomycin used as control was obtained from Boehringer Mannheim (Germany). Amphomycin can be obtained as fine chemical therefrom.

TABLE 2

A 1427 substances: in vitro activity (AB spectrum); concentration in μg/ml

| A 1437 A | 0.391 | 0.781 | 0.391 | 1.56 | 0.391 | 3.13 |
|---|---|---|---|---|---|---|
| A 1437 B | 0.098 | 0.195 | 0.098 | 0.195 | 0.049 | 0.391 |
| A 1437 C | 0.195 | 0.781 | 0.391 | 3.13 | 0.781 | 3.13 |
| A 1437 D | 0.049 | 0.195 | 0.049 | 0.781 | 0.391 | 0.781 |
| A 1437 E | 0.098 | 0.195 | 0.094 | 0.098 | 0.025 | 0.195 |
| A 1437 F | 0.098 | 0.391 | 0.195 | 1.56 | 0.781 | 1.56 |
| A 1437 G | 0.098 | 0.195 | 0.049 | 0.088 | 0.025 | 0.195 |
| A 1437 H | 0.049 | 0.098 | 0.049 | 0.195 | 0.049 | 0.195 |
| Amphomycin | 0.195 | 0.781 | 0.391 | 1.56 | 0.391 | 1.56 |

A 1437 substances: in vitro activity (vancomycin-resistant strains); concentration in μg/ml

| | Enterococcus faecium VR1 | Enterococcus faecium VR2 | Streptococcus pyogenes |
|---|---|---|---|
| A 1437 A | | not determined | |
| A 1437 B | 1 | 1 | 0.5 |
| A 1437 C | 4 | 4 | 4 |

TABLE 2-continued

| A 1437 D | 2 | 2 | 1 |
|---|---|---|---|
| A 1437 E | 4 | 4 | 1 |
| A 1437 F | 4 | 4 | 1 |
| A 1437 G | 0.25 | 0.25 | 0.125 |
| A 1437 H | 1 | 1 | 0.5 |
| Amphomycin | 4 | 4 | 2 |

The compounds K, L and M have an in vitro activity comparable with that of compounds A–H.

Example 11a: Characterization of A 1437 D

The lipopeptide A 1437 D is isolated as amorphous solid
Optical rotation: +35° (c=0.1; methanol)
HPLC: retention time: 15.1 minutes

| Amino acids: | 2 aspartic acids |
|---|---|
| | 1 asparagine |
| | 1 β-methylaspartate |
| | 2 glycine |
| | 2 2,3-diaminobutyric acid |
| | 1 proline |
| | 1 pipecolic acid |
| | 1 valine |

FAB-MS: m/e=1303.6952 $[(M+H)^+]$
Molecular mass: 1302.6884 ($C_{59}H_{94}N_{14}O_{19}$)
CID-MS: m/z=356, 491, 517, 520, 741, 761, 938, 982
IR (KBr): ν=3420 (br) $cm^{-1}$, 2930, 1660, 1530, 1450, 1400.

Example 11b: Characterization of A 1437 B

The lipopeptide A 1437 B is isolated as amorphous solid
Optical rotation: +27° (c=0.1; methanol)
HPLC: retention time: 12.8 minutes

| Amino acids: | 3 aspartic acids |
|---|---|
| | 1 β-methylaspartate |
| | 2 glycine |
| | 2 2,3-diaminobutyric acid |
| | 1 proline |
| | 1 pipecolic acid |
| | 1 valine |

FAB-MS: m/e=$[(M+H)^+]$
Molecular mass: 1303 ($C_{59}H_{93}N_{13}O_{20}$)
CID-MS: m/z=356, 407, 518, 521, 741, 762, 938, 982
IR (KBr): ν=3420 (br) $cm^1$, 2925, 1650, 1535, 1450, 1400.

Example 11c: Characterization of A 1437 C

The lipopeptide A 1437 C is isolated as amorphous solid
Optical rotation: +30° (c=0.1; methanol)
HPLC: retention time: 14.1 minutes

| Amino acids: | 2 aspartic acids |
|---|---|
| | 1 asparagine |
| | 1 β-methylaspartate |
| | 2 glycine |
| | 2 2,3-diaminobutyric acid |
| | 1 proline |
| | 1 pipecolic acid |
| | 1 valine |

Molecular mass: 1288 ($C_{58}H_{92}N_{14}O_{19}$)
CID/MS: m/z=356, 392, 503, 741, 747, 938, 981
IR (KBr): ν=3420 (br) cm$^{-1}$, 2930, 1660, 1530, 1450, 1400.

Example 11d: Characterization of A 1437 A

The lipopeptide A 1437 A is isolated as amorphous solid
Optical rotation: +30° (c=0.1; methanol)
HPLC: retention time: 11.8 minutes

| Amino acids: | 3 aspartic acids |
| --- | --- |
| | 1 β-methylaspartate |
| | 2 glycine |
| | 2 2,3-diaminobutyric acid |
| | 1 proline |
| | 1 pipecolic acid |
| | 1 valine |

Molecular mass: 1289 ($C_{58}H_{91}N_{13}O_{20}$)
CID-MS: m/z=356, 478, 504, 507, 741, 748, 938, 981
IR (KBr): ν=3420 (br) cm$^{-1}$, 2925, 1650, 1535, 1400

Example 11e: Characterization of A 1437 F

The lipopeptide A 1437 F is isolated as amorphous solid
Optical rotation: +31° (c=0.1; methanol)
HPLC: retention time: 13.8 minutes

| Amino acids: | 2 aspartic acids |
| --- | --- |
| | 1 asparagine |
| | 1 β-methylaspartate |
| | 2 glycine |
| | 2 2,3-diaminobutyric acid |
| | 1 proline |
| | 1 pipecolic acid |
| | 1 valine |

Molecular mass: 1288 ($C_{58}H_{92}N_{14}O_{19}$)
CID-MS: m/z=356, 392, 503, 506, 741, 747, 938, 981
IR (KBr): ν=3420 (br) cm$^{-1}$, 2930, 1660, 1530, 1450, 1400.

Example 11f: Characterization of A 1437 E

The lipopeptide A 1437 E is isolated as amorphous solid
RPLC: retention time: 11.5 minutes

| Amino acids: | 3 aspartic acids |
| --- | --- |
| | 1 β-methylaspartate |
| | 2 glycine |
| | 2 2,3-diaminobutyric acid |
| | 1 proline |
| | 1 pipecolic acid |
| | 1 valine |

Molecular mass: 1289 ($C_{58}H_{91}N13O_{20}$)
CID-MS: m/z=356, 393, 504, 507, 741, 748, 938, 981
IR (KBr): ν=3420 (br) cm$^{-1}$, 2925, 1650, 1535, 1450, 1400.

Example 11g: Characterization of A 1437 H

The lipopeptide A 1437 H is isolated as amorphous solid
Optical rotation: +32° (c=0.1; methanol)
HPLC: retention time: 15.9 minutes

| Amino acids: | 2 aspartic acids |
| --- | --- |
| | 1 asparagine |
| | 1 β-methylaspartate |
| | 2 glycine |
| | 2 2,3-diaminobutyric acid |
| | 1 proline |
| | 1 pipecolic acid |
| | 1 valine |

Molecular mass: 1316 ($C_{60}H_{96}N_{14}O_{19}$)
CID-MS: m/z=356, 420, 531, 534, 741, 775, 938, 981
IR (KBr): ν=3420 (br) cm$^{-1}$, 2930, 1660, 1530, 1450, 1400.

Example 11h: Characterization of A 1437 G

The lipopeptide A 1437 G is isolated as amorphous solid
Optical rotation: +34° (c=0.1; methanol)
HPLC: retention time: 13.6 minutes

| Amino acids: | 3 aspartic acids |
| --- | --- |
| | 1 β-methylaspartate |
| | 2 glycine |
| | 2 2,3-diaminobutyric acid |
| | 1 proline |
| | 1 pipecolic acid |
| | 1 valine |

Molecular mass: 1317 ($C_{60}H_{95}N_{13}O_{20}$)
CID-MS: m/z=356, 421, 532, 535, 741, 776, 938, 981
IR (KBr): ν=3420 (br) cm$^{-1}$, 2925, 1650, 1535, 1450, 1400.

Example 11i: Characterization of A 1437 K

The lipopeptide A 1437 K is isolated as amorphous solid
HPLC: Retention time: 12.5 minutes

| Amino acids: | 3 aspartic acids |
| --- | --- |
| | 1 β-methylaspartate |
| | 2 glycine |
| | 2 2,3-diaminobutyric acid |
| | 1 proline |
| | 1 pipecolic acid |
| | 1 valine |

FAB-MS: m/e=[(M+H)$^+$]
Molecular mass: 1299 ($C_{58}H_{91}N_{13}O_{20}$)
CID-MS: m/z=393, 504, 507, 741, 748, 938, 981
IR (KBr): ν=3420 (br) cm$^{-1}$, 2925, 1650, 1535, 1450, 1400

Example 11j: Characterization of A 1437 L

The lipopeptide A 1437 L is isolated as amorphous solid
HPLC: Retention time: 13.0 minutes

| Amino acids: | 3 aspartic acids |
| --- | --- |
| | 1 β-methylaspartate |
| | 2 glycine |
| | 2 2,3-diaminobutyric acid |
| | 1 proline |
| | 1 pipecolic acid |
| | 1 valine |

FAB-MS: m/e=[(M+H)$^+$]
Molecular mass: 1289 ($C_{59}H_{93}N13O_{20}$)
CID-MS: m/z=407, 518, 741, 761, 938, 981
IR (KBr): ν=3420 (br) cm$^{-1}$, 2925, 1650, 1535, 1450, 1400.

Example 11k: Characterization of A 1437 M

The lipopeptide A 1437 M is isolated as amorphous solid
HPLC: Retention time: 9.8 minutes

| Amino acids: | 3 aspartic acids |
| --- | --- |
| | 1 β-methylaspartate |
| | 2 glycine |
| | 2 2,3-diaminobutyric acid |
| | 1 proline |
| | 1 pipecolic acid |
| | 1 valine |

FAB-MS: m/e=[(M+H)$^+$]
Molecular mass: 1275 ($C_{57}H_{89}N_{13}O_{20}$)
CID-MS: m/z=379, 490, 493, 724, 741, 938, 981
IR (KBr): ν=3420 (br) cm$^{-1}$, 2925, 1650, 1535, 1450, 1400.

Example 12: C13 chem. shifts

The table shows the C13 chem. shifts of the CH signals of A 1437 B

| Assign. | Dab | Gly | MeAsp | Gly | Asp | Asp | Asp | Dab | Val | Pro | Pip |
| --- | --- | --- | --- | --- | --- | --- | --- | --- | --- | --- | --- |
| NH/Cα | 8.30 | 8.43 | 8.19 | 8.12 | 8.09 | 7.96 | 8.15 | 7.87 | 7.30 | 4.13 | 4.62 |
| α | 56.00 | 44.60 | 41.20 | 44.70 | 52.00 | 53.10 | 53.00 | 55.60 | 59.20 | 62.40 | 56.80 |
| β | 50.10 | | 14.40 | | 36.10 | 35.60 | 36.30 | 47.80 | 31.30 | 30.80 | 27.20 |
| z | 16.00 | | | | | | | 20.10 | 18.9 | 26.00 | 20.60 |
| | | | | | | | | | 19.7 | | |
| δ | | | | | | | | | | 49.40 | 24.90 |
| γ | | | | | | | | | | | 45.00 |

In order for comparison with the $^1$H data to be possible, the NH chem. shifts of the NH signals, and for Pip and Pro the CaH shifts of the corresponding spin systems, have also been indicated.

What is claimed is:
1. Lipopeptides of the formula I

R$^1$—R$^2$-Dab-Pip-MeAsp-Asp-Gly-Asp-Gly-Dab-Val-Pro    I

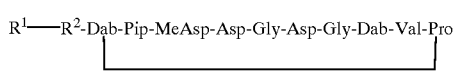

in which R$^1$ is a singly or multiply unsaturated branched or unbranched or a saturated branched or unbranched fatty acid with a chain length of 12, 13, 14, or 15 carbon atoms and R$^2$ is Asn.

2. The lipopeptide of the formula I as claimed in claim 1, wherein the lipopeptide is:

a) aiC$_{13}$-fatty acid-Asn-Dab-Pip-MeAsp-Asp-Gly-Asp-Gly-Dab-Val-Pro b) iC$_{14}$-fatty acid-Asn-Dab-Pip-MeAsp-Asp-Gly-Asp-Gly-Dab-Val-Pro;

c) iC$_{13}$-fatty acid-Asn-Dab-Pip-MeAsp-Asp-Gly-Asp-Gly-Dab-Val-Pro;

or d) aiC$_{15}$-fatty acid-Asn-Dab-Pip-MeAsp-Asp-Gly-Asp-Gly-Dab-Val-Pro.

3. The lipopeptide of the formula I as claimed in claim 1, in which R$_1$ is selected from the group consisting of:

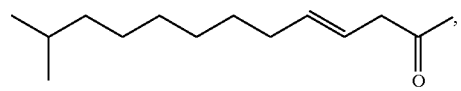

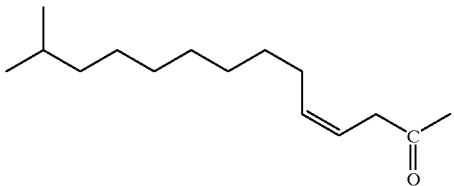

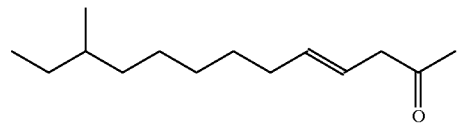

and

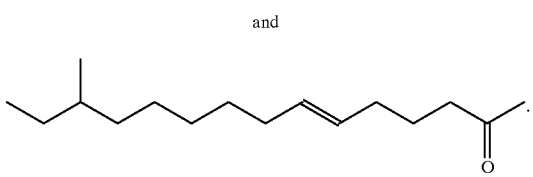

4. A process for the preparation of one or more lipopeptides of the formula I as claimed in claim 1 or 2, which comprises fermenting Actinoplanes sp. in a culture medium until one or more lipopeptides accumulate in the culture medium and purifying one or more lipopeptides from the culture medium.

5. The process as claimed in claim 4, wherein the purification takes place by acid precipitation of the lipopeptides from the culture medium, wherein the acids range from pH 0.5 to pH 4.

6. The process as claimed in claim 5, further comprising the purification of the acid precipitated lipopeptides by chromatography on an anion exchange column or a hydrophobic matrix.

7. The process as claimed in claim 4, wherein Actinoplanes sp. DSM 7358 is fermented.

8. A pharmaceutical composition containing one or more lipopeptides of the formula I as claimed in claim 1 and a pharmaceutical vehicle.

9. A method of using a lipopeptide of the formula I as claimed in claim 1 comprising administering said lipopeptide as an antibiotic against Gram-positive bacteria.

10. The method of claim 9 wherein said bacteria is a glycopeptide-resistant bacteria.

11. Actinoplanes sp. DSM 7358.

12. A lipopeptide of the formula I as claimed in claim 1 in which

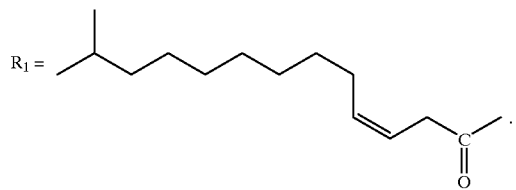

* * * * *